United States Patent
Suda (10) Patent No.: US 11,065,014 B2
(45) Date of Patent: Jul. 20, 2021

(54) PUNCTURE TOOL GUIDING DEVICE

(71) Applicant: KABUSHIKIKAISHA KKYSS, Hokkaido (JP)

(72) Inventor: Kota Suda, Hokkaido (JP)

(73) Assignee: KABUSHIKIKAISHA KKYSS, Hokkaido (JP)

( * ) Notice: Subject to any disclaimer, the term of this patent is extended or adjusted under 35 U.S.C. 154(b) by 0 days.

(21) Appl. No.: 16/756,017

(22) PCT Filed: Dec. 6, 2018

(86) PCT No.: PCT/JP2018/044866
§ 371 (c)(1),
(2) Date: Apr. 14, 2020

(87) PCT Pub. No.: WO2019/138742
PCT Pub. Date: Jul. 18, 2019

(65) Prior Publication Data
US 2020/0237383 A1    Jul. 30, 2020

(30) Foreign Application Priority Data

Jan. 12, 2018  (JP) .............................. JP2018-003772

(51) Int. Cl.
*A61B 17/17*   (2006.01)
*A61B 17/16*   (2006.01)
*A61B 17/70*   (2006.01)

(52) U.S. Cl.
CPC ...... *A61B 17/1757* (2013.01); *A61B 17/1671* (2013.01); *A61B 17/1703* (2013.01); *A61B 17/7002* (2013.01)

(58) Field of Classification Search
CPC .................. A61B 17/1757; A61B 17/1671
See application file for complete search history.

(56) References Cited

U.S. PATENT DOCUMENTS 6,143,012 A * 11/2000 Gausepohl ......... A61B 17/1604
606/185
8,663,233 B2 * 3/2014 Suda .................. A61B 17/1757
606/96

(Continued)

FOREIGN PATENT DOCUMENTS

| JP | 2009-261485 | 11/2009 |
| JP | 2013-34777 | 2/2013 |
| WO | 2006/038959 | 4/2006 |

OTHER PUBLICATIONS

International Search Report dated Feb. 19, 2019 in International (PCT) Application No. PCT/JP2018/044866.

*Primary Examiner* — Christian A Sevilla
(74) *Attorney, Agent, or Firm* — Wenderoth, Lind & Ponack, L.L.P.

(57) ABSTRACT

A device for guiding a puncture tool to form a pilot hole through which a pedicle screw is buried in a pedicle, the device including a linear reference pin disposed forward from a rear side of a spine toward a target point of a pedicle base; a tubular sleeve having a sleeve central axis disposed at a predetermined insertion angle to the reference pin, and having a distal end open toward the target point and through which the puncture tool is passed and guided; and a rod member that couples a proximal side of the reference pin to the sleeve and maintains the sleeve central axis at the predetermined insertion angle to the reference pin. Plural slits are formed with a cutting direction orthogonal to the reference pin. A shape of a slit portion is recognized by an X-ray fluoroscopic image, and the puncture tool can be easily guided.

5 Claims, 6 Drawing Sheets

(56) References Cited

U.S. PATENT DOCUMENTS

| | | | |
|---|---|---|---|
| 10,687,845 B2* | 6/2020 | Geist | A61B 10/025 |
| 2006/0084977 A1* | 4/2006 | Lieberman | A61B 17/8863 606/60 |
| 2012/0197320 A1* | 8/2012 | Bereczki | A61B 17/32053 606/86 R |
| 2016/0030067 A1* | 2/2016 | Frey | A61B 17/15 606/86 A |

* cited by examiner

PUNCTURE TOOL GUIDING DEVICE

TECHNICAL FIELD

The present invention relates to a puncture tool guiding device to accurately guide an inserting position and direction of a puncture tool, when a pilot hole, through which a pedicle screw for use in spinal fusion that is a surgical operation of a spine is buried, is formed in a vertebra with the puncture tool.

BACKGROUND ART

In fusion of a cervical spine or the like, a technique of burying a pedicle screw in a spine is frequently adopted. This pedicle screw is buried by inserting a puncture tool such as a probe to form a pilot hole in advance, and screwing the pedicle screw into the pilot hole.

Now, important organs such as a spinal cord, a nerve root, a blood vessel and an internal organ are located densely around the spine. In particular, there is concern that, when the probe or the like that is the puncture tool is inserted into a wrong position to form the pilot hole in the cervical spine, serious disability is caused in the above organ. Therefore, it is necessary to determine an accurate inserting position and direction when the pilot hole is formed by inserting the puncture tool.

In a related art, a front image and a side image of a spine are projected with an X-ray device, and a position of a pedicle into which a probe is inserted is confirmed, to insert the probe without any guide. However, there is a problem that such an operation of the probe without any guide is greatly influenced by an amount of experience and a skill of an operator and that variation in insertion accuracy is generated. Furthermore, even after the probe is accurately inserted, there is still concern that an angle shifts and deviates during tapping or screw insertion.

In Patent Literature 1 disclosed by the present applicants, there is disclosed a puncture tool guiding device including a reference pin to be inserted forward from a rear side of a spine into a pedicle base and to serve as a reference, and an arm body extending laterally from a proximal side of the reference pin. In the arm body, there are formed a plurality of guide holes that are open toward a position of a pointed end of the reference pin, to guide a puncture tool, and the plurality of guide holes are formed radially about the position of the pointed end of the reference pin.

According to the puncture tool guiding device of Patent Literature 1, when the puncture tool is passed through the guide hole formed in the arm body, the puncture tool can be accurately guided at an insertion angle. Furthermore, since the plurality of guide holes are radially arranged about the position of the pointed end of the reference pin, the insertion angle of the puncture tool can be changed in accordance with a tilt angle of a pedicle, and the puncture tool can be inserted into the pedicle at an appropriate tilt angle.

In Patent Literature 2 similarly disclosed by the present applicants, there is disclosed a puncture tool including a puncture needle to form a pilot hole, and a reference bar that is provided at a predetermined angle from the puncture needle and serves as a reference to guide the puncture needle to a desired position and at a desired angle. At a proximal end and a distal end of the reference bar, a first auxiliary bar and a second auxiliary bar protruding in a direction orthogonal to the reference bar are provided, and both the auxiliary bars protrude in directions opposite to each other with the reference bar therebetween.

According to this puncture tool of Patent Literature 2, the reference bar is provided at the predetermined angle to the puncture needle, and the puncture needle is guided at a desired angle to a desired inserting position by this reference bar. Consequently, any special guide device that guides the puncture needle to a target position does not have to be separately provided, and the inserting position and direction to the pedicle can be accurately controlled with a simple configuration. Additionally, the first auxiliary bar and the second auxiliary bar are installed at the proximal end and the distal end of the reference bar. Consequently, in an X-ray fluoroscopic image of a side of a spine, the first auxiliary bar and the second auxiliary bar are linearly arranged as long as the reference bar is horizontal, and a horizontal state of the reference bar can be easily confirmed by two auxiliary bars.

Furthermore, in Patent Literature 3, there is disclosed a minimally invasive apparatus to place screws across a facet joint between a first vertebra and a second vertebra that are adjacent to each other. This apparatus includes a first wire to be inserted into a spinous process of the first vertebra, a first fixing block removably connected to the first wire, a second wire to be inserted into a transverse process of the second vertebra, and a second fixing block removably connected to the second wire. A rod member is removably connected to both of the first and second fixing blocks, and a rotary block assembly includes relatively movable first and second block members. The rod member is removably connected to the first block member, and a cannula extends from the second block member. Then, a guide wire is inserted in the cannula, and a facet screw is inserted in the cannula, to fuse the adjacent vertebrae.

CITATION LIST

Patent Literature

Patent Literature 1: Japanese Patent Laid-Open No. 2009-261485
Patent Literature 2: Japanese Patent Laid-Open No. 2013-34777
Patent Literature 3: International Publication No. WO2006038959

SUMMARY OF INVENTION

Technical Problem

Here, three axes orthogonal to one another are defined as an X-axis, a Y-axis and a Z-axis. A front-rear direction of a spine is defined as a Z-axis direction, a lateral direction of the spine is defined as an X-axis direction, and an intervertebral direction is defined as a Y-axis direction, respectively. Then, in a guiding device of Patent Literature 1, a predetermined angle can be accurately grasped on a plane formed by a reference pin and a guide hole of an arm body (a plane including the X-axis and the Z-axis), but a skill of an operator is required to grasp an accurate position in the Y-axis direction. In Patent Literature 3, accurate positioning in the Y-axis direction requires skill in the same manner as in Patent Literature 1.

On the other hand, in Patent Literature 2, a guiding device is not required separately from a puncture tool, but a reference bar protrudes in an X-axis direction, at a predetermined angle to an inserting direction of a puncture needle. Furthermore, first and second auxiliary bars protrude in the Y-axis direction orthogonal to the reference bar, and hence there is possibility that a cut region in skin enlarges. Consequently, there is desired appearance of a puncture tool guiding device in which a further minimally invasive treatment is possible.

The present invention has been made in view of the above problems, and an object thereof is to provide a puncture tool guiding device capable of more easily guiding a puncture tool.

Solution to Problem

To achieve the above object, according to one aspect of the present invention, there can be provided a puncture tool guiding device for guiding a puncture tool to form a pilot hole through which a pedicle screw is buried in a pedicle, the puncture tool guiding device including: a linear reference pin that is disposed forward from a rear side of a spine toward a target point of a pedicle base and serves as a reference; a tubular sleeve having a sleeve central axis disposed at a predetermined insertion angle to the reference pin, and having a distal end that is open toward the target point and through which the puncture tool is passed and guided; and a rod member that couples a proximal side of the reference pin to the sleeve and maintains the sleeve central axis at the predetermined insertion angle to the reference pin, wherein a slit for confirming, by an X-ray fluoroscopic image, whether or not the puncture tool guiding device is installed accurately on the pedicle is formed in a side surface of the sleeve, and the slit is formed such that a cutting direction of the slit is orthogonal to the reference pin.

Figure 1:
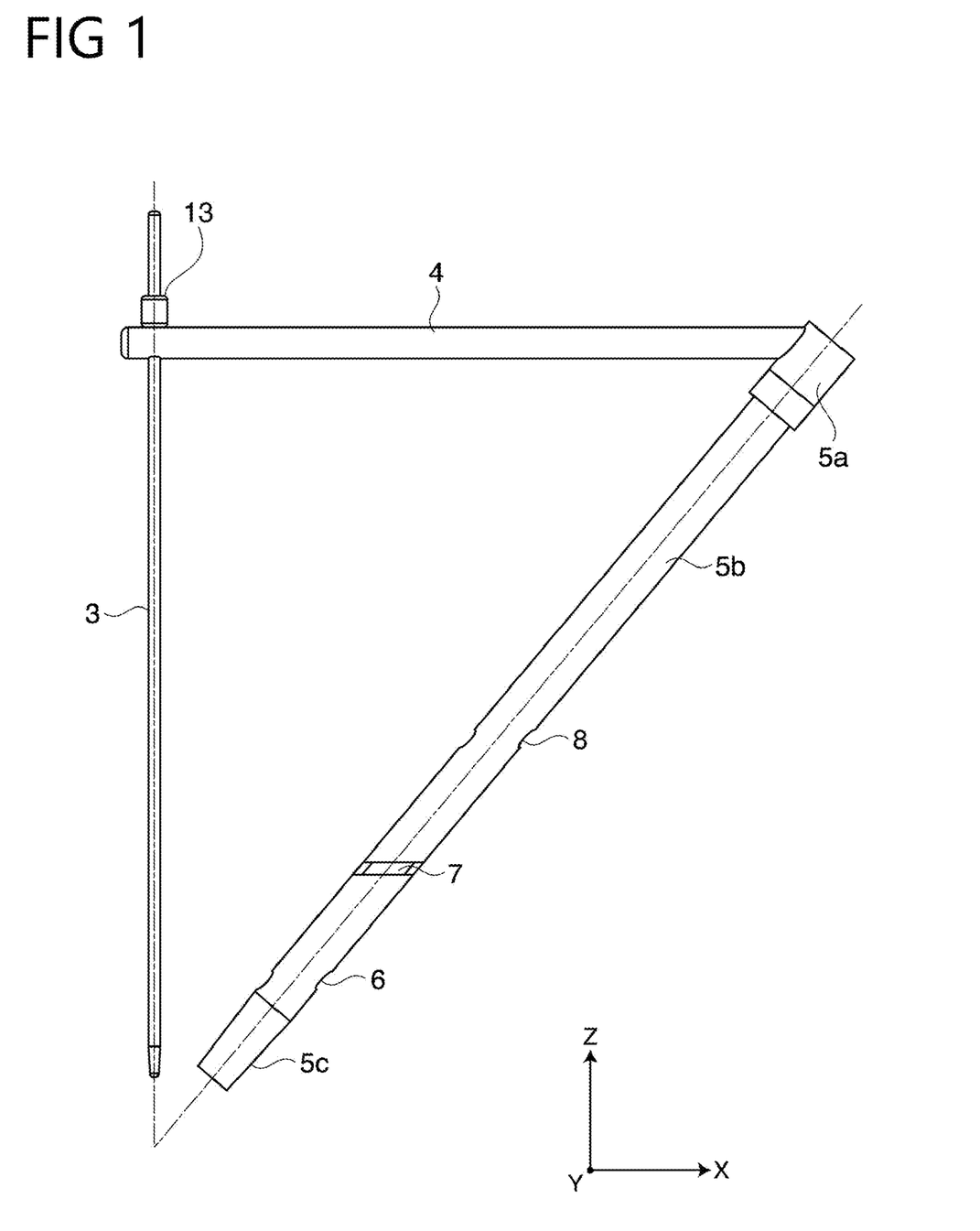
FIG. 1 is a front view of a puncture tool guiding device showing an embodiment of the present invention.
Figure 2:
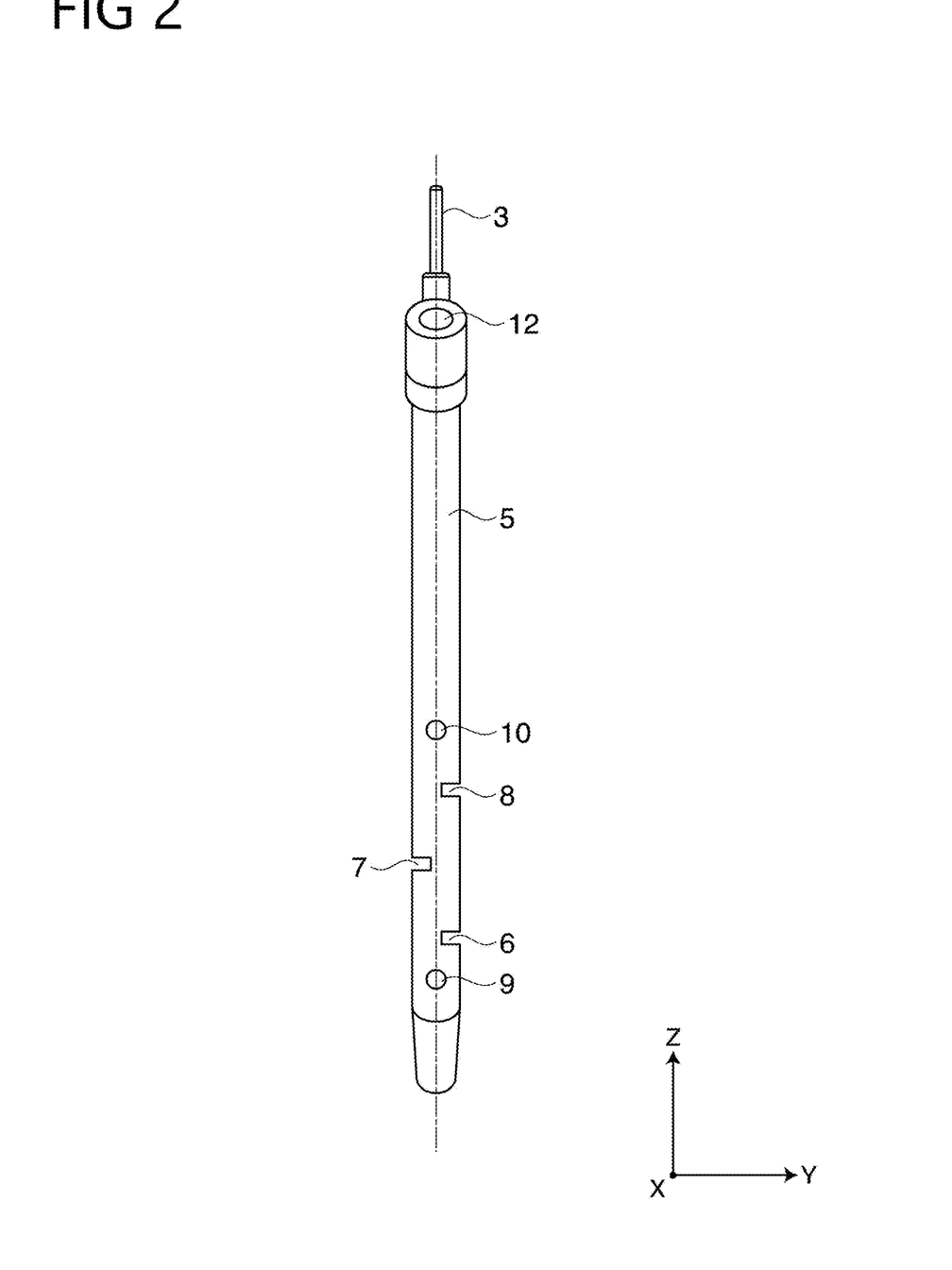
FIG. 2 is a side view of the puncture tool guiding device.

In other words, the cutting direction of the slit is a direction orthogonal to the linear reference pin. Furthermore, a number of the slits is not limited to one, and according to a preferable aspect, a plurality of slits are formed at intervals in an axial direction of the sleeve. In this case, a cross section of the slit orthogonal to the cutting direction may be formed in a shape having a rectangular cut recess. Additionally, as shown in FIG. 2, for the plurality of slits, three or more slits may be provided at intervals in the axial direction of the sleeve, and the slits may be arranged in a tubular wall of the sleeve in a staggered manner in the axial direction with the central axis of the sleeve therebetween. Furthermore, in addition to the above configuration, in the sleeve, a through hole extending through the sleeve in parallel with the cutting direction of the slit may be formed separately from the slit.

Advantageous Effects of Invention

According to the present invention, when a puncture tool is passed through a guide hole formed in a sleeve, the tool can be accurately guided at an insertion angle. In particular, a slit is formed in the sleeve, and hence, an arbitrary angle can be seen by X-ray fluoroscopy. For example, an angle of the sleeve in which slits are formed is set to 40 degrees in advance and the angle is accurately 40 degrees. In this case, when seen by the X-ray fluoroscopy, each slit is aligned and can be clearly seen through the sleeve. When the angle shifts from 40 degrees, the width of each slit looks small, or any slits cannot be seen at all. That is, the angle can be seen by the X-ray fluoroscopy.

Furthermore, in the sleeve, when through holes formed in opposite tubular walls are linearly superimposed, the holes can be seen through the sleeve by fluoroscopy in an X-axis direction. Consequently, rotation of the sleeve can be seen, and an accurate inserting position can be grasped also in a Y-axis direction.

DESCRIPTION OF EMBODIMENTS

Hereinafter, an embodiment of the present invention will be described with reference to the drawings. A puncture tool guiding device 1 in the present embodiment guides a puncture tool 2 to form a pilot hole through which a pedicle screw is buried in a pedicle.

The puncture tool guiding device 1 includes a reference pin 3 that is disposed forward from a rear side of a spine toward a target point S on a pedicle base and serves as a reference, a linear rod member 4 having one end portion located on a proximal side of the reference pin 3 and another end portion laterally extending, and a tubular sleeve 5 installed in the other end portion of the rod member 4 at a first predetermined angle θ1 to the rod member 4, and having a distal end that is open toward the target point S (that may be hereinafter referred to simply as "point S") and through which the puncture tool 2 is passed and guided.

Furthermore, a plurality of slits 6, 7 and 8 are formed in a side surface of the sleeve 5 in a cutting direction at the same angle as the first predetermined angle θ1 to a central axis of the sleeve 5. In other words, the plurality of slits 6, 7 and 8 parallel to the linear rod member 4 are formed at intervals in an axial direction of the sleeve 5. The slits 6, 7 and 8 are arranged in a tubular wall of the sleeve 5 in a staggered manner in the axial direction with the central axis of the sleeve therebetween. Furthermore, two upper and lower through holes 9 and 10 extending through the sleeve in parallel with the cutting direction of the slits 6, 7 and 8 are formed in the sleeve 5 separately from the plurality of slits 6, 7 and 8.

There are not any special restrictions on a material of the reference pin 3, and in the present example, the reference pin made of stainless steel is adopted. The reference pin is linearly formed, and a distal side of the pin has a diameter smaller than a diameter of another portion of the pin. The reference pin of the present example is set to a length for use in attaching the reference pin to a vertebral arch from a rear side of the spine. In another aspect, the reference pin 3 may be set to a length such that the pin can be inserted from the rear side of the spine through the vertebral arch into a pedicle base, and the reference pin 3 inserted into a pedicle for use may be adopted.

The reference pin 3 is inserted in a vertical hole perforated in a direction orthogonal to an axial direction of the rod member 4 at one end of the rod member 4, and retained with an annular proximal side retaining member 10. The retaining member 13 is movable and fixable along an axial direction of the reference pin 3 in accordance with an insertion length of the reference pin 3 into a vertebral arch side. As for the reference pin 3, a plurality of types of reference pins having different insertion lengths into the vertebral arch may be prepared, and the appropriate pin may be removably mounted to the rod member 4. The reference pin 3 in the present example is set to a small diameter of about 1.8 mm, but the diameter is not limited to this example.

There are not any special restrictions on a material of the rod member 4, but in the present example, the rod member made of stainless steel is adopted. The rod member is linearly formed of a bar-like member or a tubular member. The one end of the rod member 4 has the vertical hole perforated in the direction orthogonal to the axial direction of the rod member, and the reference pin 3 is passed through this vertical hole in an up-down direction. At the other end of the rod member 4, there is a fixed sleeve 5 extending obliquely downward to a reference pin 3 side with the first predetermined angle θ1.

There are not any special restrictions on a material of the sleeve 5, but in the present example, a tubular member made of stainless steel is adopted. An interior of a tube of the sleeve 5 serves as a guide hole 12 that is open toward the target point S of the pedicle base. The guide hole 12 guides the puncture tool 2 in an inserting direction. The guide hole 12 is formed in a size such that the puncture tool 2 such as a drill can be inserted in the hole, and the size is preferably substantially equal to a diameter of the puncture tool 2. Furthermore, the guide hole 12 is formed in a round shape, and the shape may be changed in accordance with a cross-sectional shape of the puncture tool 2. Additionally, the guide hole 12 is required to have at least a length to such an extent that the guide hole can support the puncture tool 2 in the inserting direction.

The sleeve 5 includes a large diameter section 5a fixed to the rod member 4, a main body section 5b having a diameter slightly smaller than that of the large diameter section 5a and extending obliquely downward to the reference pin side continuously with the large diameter section, and a distal section 5c including a distal end having a thickness smaller than that of the main body section 5b in a tapered manner. Furthermore, there is prepared the sleeve having a second predetermined angle θ2 as an angle at which an extension line of the sleeve 5 in the axial direction intersects an extension line of the reference pin 3.

Here, the linear reference pin 3 and the linear rod member 4 intersect at right angles (90 degrees). Consequently, the second predetermined angle θ2 and the first predetermined angle θ1 are in a relation of complementary angles (θ1+θ2=90 degrees). As for the second predetermined angle θ2, for example, there are about seven types of angles that differ every five degrees, e.g., 30 degrees, 35 degrees, 40 degrees, 45 degrees, 50 degrees, 55 degrees and 60 degrees, and the puncture tool guiding devices 1 including the sleeves 5 having the predetermined angles θ2 are prepared. Among these devices, the guiding device 1 having the optimum predetermined angle θ2 is selected, and the puncture tool 2 is passed through the sleeve 5 of the device. Then, the optimum insertion angle θ2 can be selected in accordance with a shape of a vertebra. As the puncture tool 2, a tool having a puncture function, such as a drill, a tap, a screw or the like, is used.

It can be considered that the cutting direction of the plurality of slits 6, 7 and 8 formed in the sleeve 5 at intervals is a direction orthogonal to the linear reference pin 3. When three slits are first, second and third slits in order from a distal side of the sleeve, in FIG. 2, the first slit 6 and the third slit 8 are formed in an elongate shape in a right side surface of the sleeve 5, and the second slit 7 is formed at an intermediate position between the first slit 6 and the third slit 8. Note that a number of the slits is not limited to three as described above, and may be one or more.

Here, three axes orthogonal to one another are defined as an X-axis, a Y-axis and a Z-axis, and a front-rear direction of the spine is defined as a Z-axis direction, a lateral direction of the spine is defined as an X-axis direction, and an intervertebral direction is defined as a Y-axis direction, respectively. Then, the linear reference pin 3 is disposed in the Z-axis direction, and the linear rod member 4 is disposed in the X-axis direction. When the slits 6, 7 and 8 arranged in a horizontal direction are seen, as shown in FIG. 2, each slit is seen in a shape having a rectangular cut recess. Furthermore, as shown in FIG. 2, two upper and lower through holes 9 and 10 are seen as respective through holes 9 and 10 formed in opposite tubular walls and extending through the walls in the X-axis direction. In the present example, the through holes 9 and 10 are arranged above and below the slits 6, 7 and 8 and spaced apart from the slits 6 and 8, respectively.

Figure 3:
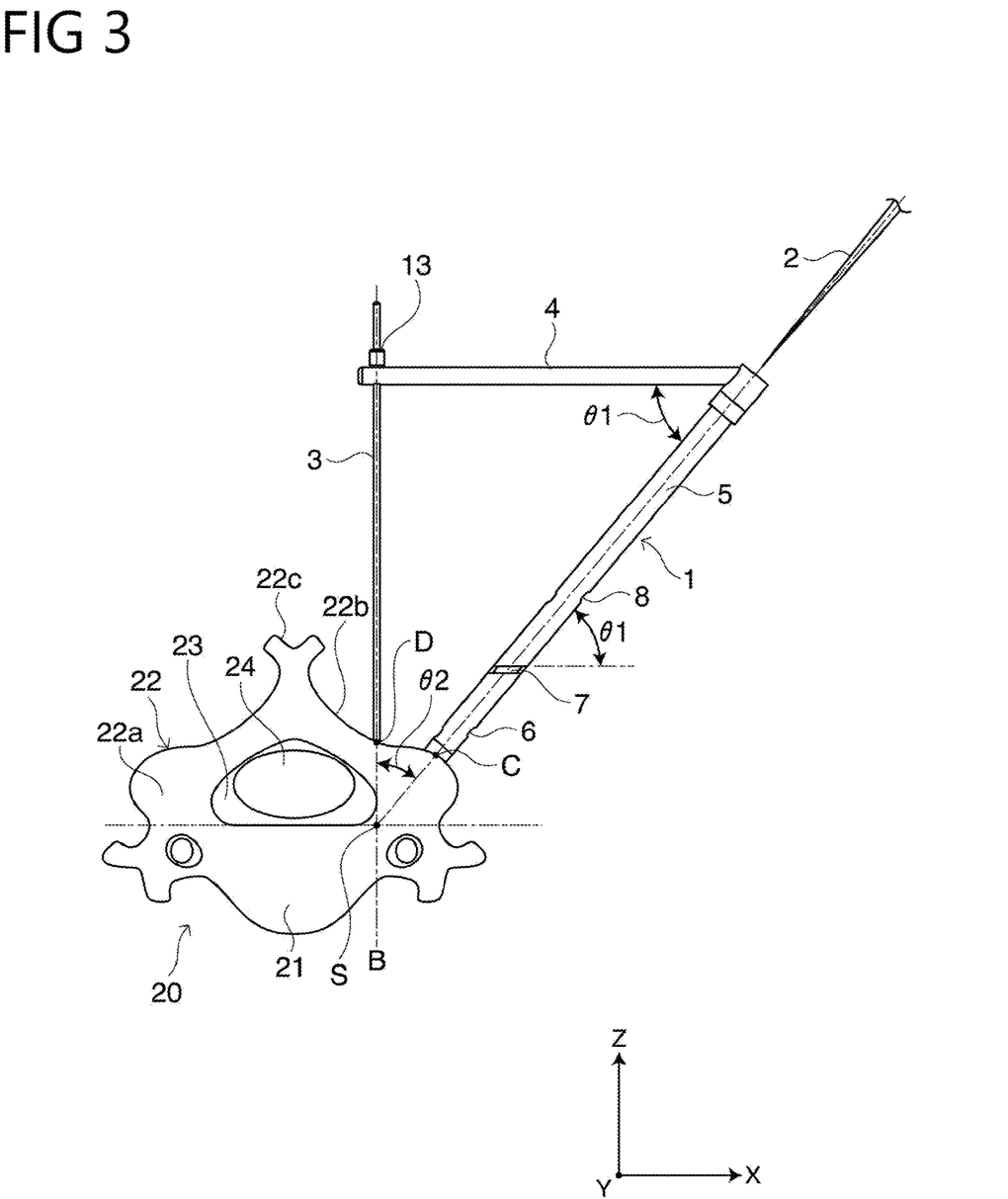
FIG. 3 is a conceptual view when the puncture tool guiding device is for use in a spine.

Description will be made as to a case where a surgical operation of spinal fusion by backward deployment is performed by the using puncture tool guiding device 1 of the above configuration. First, a cross-sectional structure of the vertebra will be described with reference to FIG. 3. As shown in FIG. 3, vertebra 20 is constituted of a vertebral body 21 located in front and a vertebral arch 22 located in rear. The vertebral arch 22 is a scale-like part exiting backward from the vertebral body 21, and is constituted of pedicle 22a attached to the vertebral body 21 and laminae of vertebral arch 22b that are like bent plates behind the pedicle. The laminae of vertebral arch 22b join in middle and form a spinous process 22c backward. A large hole surrounded with the vertebral body 21 and the vertebral arch 22 is vertebral foramen 23, this hole is a location through which a spinal cord 24 passes, and a vertical range of foramina is referred to as a spinal canal.

In a cross-sectional image by computer tomography (CT), as shown in FIG. 3, an intersection S between a tangent line A of a back face of the vertebral body 21 and a perpendicular line B at an outer edge of the vertebral foramen 23 (the spinal canal) is indexed, and the intersection S serves as the point S that is the target point. Therefore, a straight line parallel to tilt of the pedicle 22a is drawn from the target point S, and the insertion angle θ2 of the puncture tool 2 is indexed from this straight line. The insertion angle θ2 is the second predetermined angle formed by a central axis of the puncture tool 2 and the perpendicular line B. The puncture tool guiding device 1 that matches the insertion angle θ2 is selected. The puncture tool guiding device 1 that matches the insertion angle θ2 is a device in which the second predetermined angle formed by the reference pin 3 and the central axis of the sleeve 5 serves as the insertion angle θ2.

Next, an intersection C between an extension line of a straight line that passes the point S in parallel with the tilt of the pedicle 22a and a surface of the lamina of vertebral arch 22b or the like is marked, and the intersection C is considered as an installation point of the sleeve 5. An intersection D between the perpendicular line B drawn from the target point S and the surface of the lamina of vertebral arch 22b or the like is marked, and this intersection is considered as an installation point of the reference pin 3.

Then, the puncture tool guiding device 1 in which the sleeve 5 has an appropriate tilt θ2 is selected, and the reference pin 3 is installed at the intersection D. Furthermore, the sleeve 5 is aligned with the installation point C. At this time, the sleeve 5 is installed so that the slits 6, 7 and 8 have a horizontal state and the through holes 9 and 10 are also horizontal.

In this state, the puncture tool 2 such as the tap or the screw is inserted in the sleeve 5. A mark such as a line is attached to the puncture tool 2 so that a length from a pointed end of the puncture tool 2 to the reached line B is seen by an operator. When the puncture tool 2 is inserted as much as the length indicated by the mark and the reference pin 3 is located on the line B, the pointed end of the puncture tool 2 is present on the line A in X-ray fluoroscopy, and reaches the point S having high safety.

Thus, when the point S is present on the perpendicular line (line B) of the distal end of the reference pin 3 provided at one end of the rod member 4 and a puncture tool such as the drill, the tap or the screw reaches a vertebral body rear wall (point S), the reference pin 3 is present on the spinal canal outer edge. Then, the distal end of the puncture tool 2 is located at the point S.

Figure 4A:
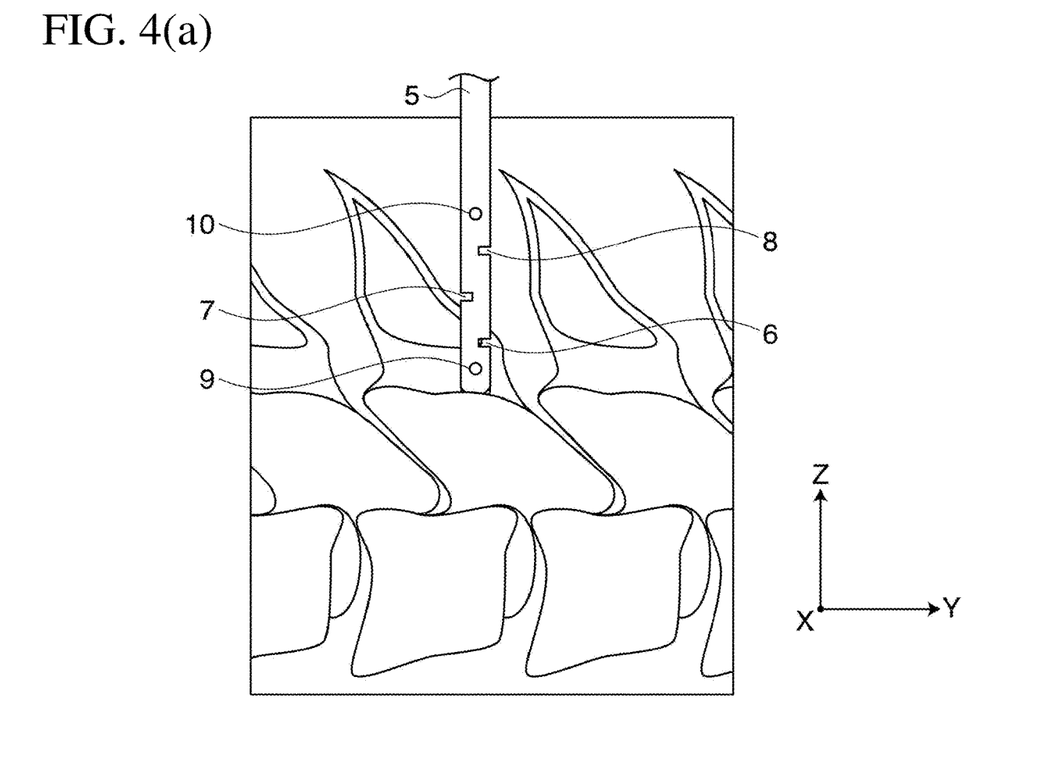
FIG. 4(a) is a radiograph showing an optimum state of an insertion angle of the puncture tool guiding device into a pedicle.
Figure 4B:
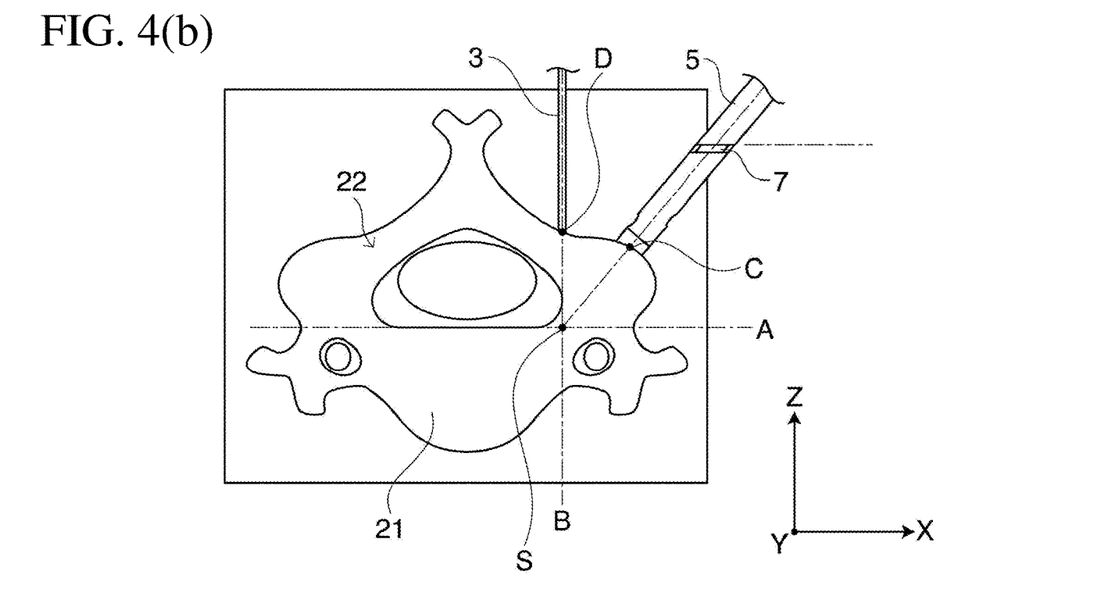
FIG. 4(b) is a cross-sectional view of a vertebra at this time by computer tomography (CT, the same as below).

FIGS. 4(a) and (b) show a state where the guiding device 1 is installed in an optimum state. As shown in the figure (a), when seen in an X-ray fluoroscopic image photographed from a side (in the X-axis direction), each cut recess of the slits 6, 7 and 8 of the sleeve 5 is aligned in the X-axis direction and can be clearly seen through the sleeve. Furthermore, the upper and lower through holes 9 and 10 can be also clearly seen through the sleeve.

Figure 5A:
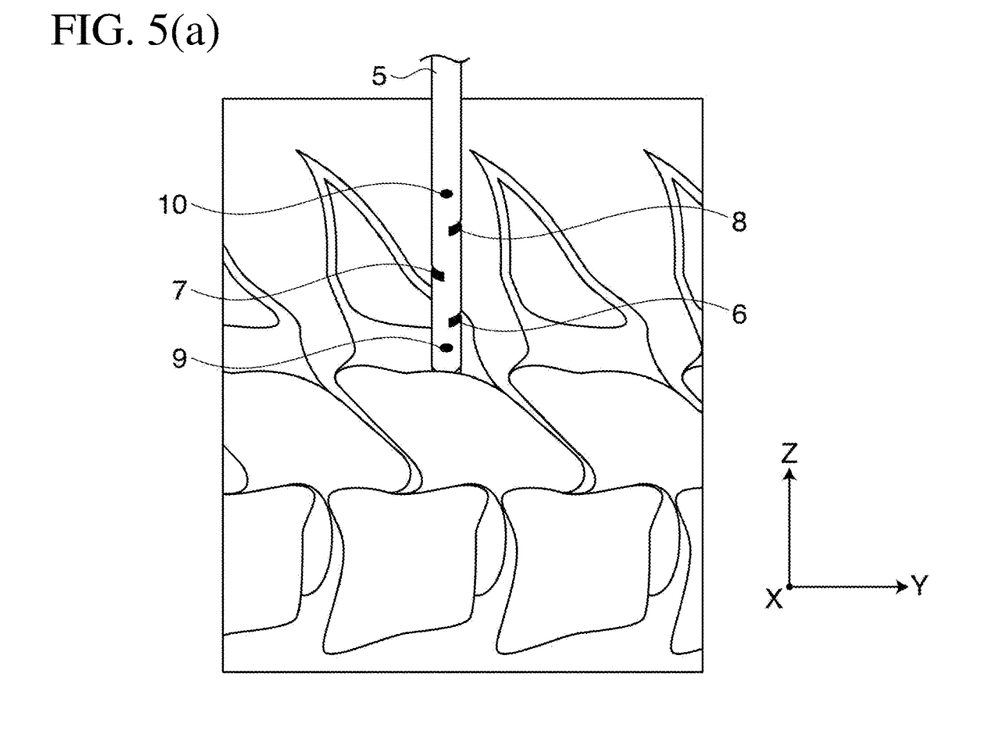
FIG. 5(a) is a radiograph showing a tilted state of the puncture tool guiding device at an inappropriate angle into the pedicle.
Figure 5B:
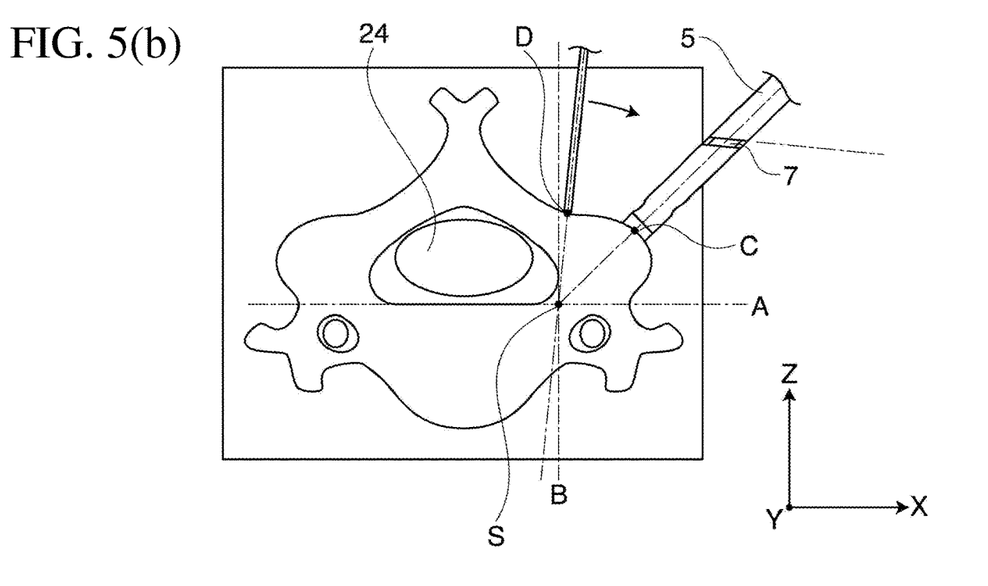
FIG. 5(b) is a cross-sectional view of the vertebra at this time by the CT.

FIGS. 5(a) and (b) show a state where the reference pin 3 shifts from the perpendicular line that passes the point S and the extension line of the central axis of the sleeve 5 shifts from the point S. In this state, as shown in FIG. 5(a), when seen in an X-ray fluoroscopic image photographed from a side (in the X-axis direction), the slits 6, 7 and 8 of the sleeve 5 tilt from a horizontal state. Consequently, each cut recess is superimposed little in the X-axis direction, and look linear. Furthermore, the upper and lower through holes 9 and 10 are superimposed little, and look like black points as shown in FIG. 5.

Figure 6A:
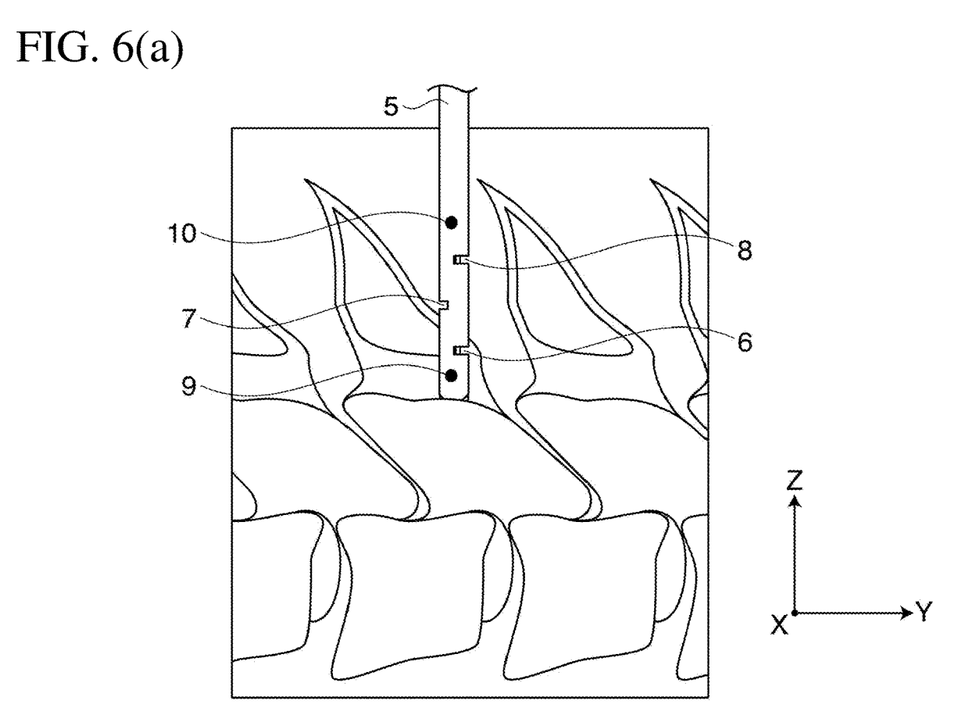
FIG. 6(a) is a radiograph when the inserted puncture tool guiding device into the pedicle is rotated.
Figure 6B:
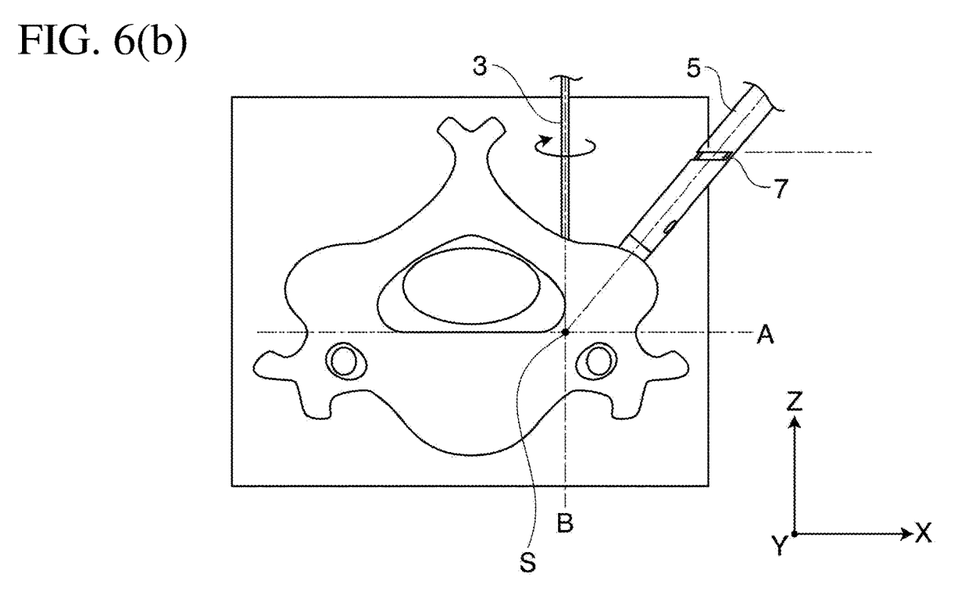
FIG. 6(b) is a cross-sectional view of the vertebra at this time by the CT.

FIGS. 6(a) and (b) show a state where the sleeve 5 is rotated about the reference pin 3. In this state, as shown in the figure (a), when seen in the X-ray fluoroscopic image photographed from the side (in the X-axis direction), left and right widths of the left and right slits 6, 7 and 8 of the sleeve 5 do not look the same. Furthermore, the upper and lower through holes 9 and 10 are superimposed little, and look like black points as in the drawing.

As described above, according to the embodiment of the present invention, the slits 6, 7 and 8 are formed in a plurality of portions of the sleeve 5, and an arbitrary angle can be seen in the X-ray fluoroscopic image. For example, the angle of the sleeve in which the slits are formed is set to the predetermined angle in advance and the predetermined angle is accurately obtained. When seen in the X-axis direction, the slits are superimposed and can be clearly seen through the sleeve. Furthermore, when the through holes 9 and 10 of the sleeve 5 are linearly aligned, the through holes can be seen through the sleeve in the X-axis direction. Consequently, a rotated state of the sleeve 5 can be distinguished and an accurate inserting position can be grasped.

Note that the present invention is not limited to the above embodiment, and needless to say, a large number of modifications and changes can be added within a scope of the present invention. For example, as the rod member 4 of the above embodiment, the linear rod member is used and adopted as one of references that determine the slit cutting direction (the direction parallel to the rod member), but the rod member is not limited to the linear rod member. A rod member having another shape, for example, a circular shape may be adopted, and another member, for example, a linear reference pin may be adopted as the fiducial reference of the cutting direction of the slit. In short, the present invention may be applied to an aspect in which a slit may be formed in a cutting direction that forms a predetermined angle to an axial direction of a sleeve and it can be confirmed by using this slit whether or not a guiding device is accurately installed. This also applies to the through holes formed above and below the slits. Furthermore, the through holes are not limited to the aspect in which the through holes are formed above and below the plurality of slits, and may be applied to an aspect where the through holes are formed among the plurality of slits.

REFERENCE SIGNS LIST 1 puncture tool guiding device
2 puncture tool
3 reference pin
4 rod member
5 sleeve
6, 7 and 8 slit
9 and 10 through hole
12 guide hole
A tangent line of a back face of a vertebral body
B perpendicular line of an outer edge of a vertebral foramen (spinal canal)
C intersection
D intersection
S target point (point S)
θ1 angle formed by axial direction of sleeve and cutting direction of slit
θ2 intersection angle between reference pin and sleeve

The invention claimed is:

1. A puncture tool guiding device for guiding a puncture tool to form a pilot hole through which a pedicle screw is buried in a pedicle, the puncture tool guiding device comprising:
   a linear reference pin that is positionable forward from a rear side of a spine toward a target point of a pedicle base and serves as a reference,
   a tubular sleeve having a sleeve central axis disposed at a predetermined insertion angle to the reference pin, and having a distal end that is open toward the target point and through which the puncture tool is passable and guidable, and
   a rod member that couples a proximal side of the reference pin to the sleeve and maintains the sleeve central axis at the predetermined insertion angle to the reference pin, wherein a slit for confirming, by an X-ray fluoroscopic image, whether or not the puncture tool guiding device is installed accurately on the pedicle is formed in a side surface of the sleeve, and the slit is formed such that a length direction of the slit is orthogonal to the reference pin.

2. The puncture tool guiding device according to claim 1, wherein a cross section of the slit orthogonal to the length direction is formed in a shape having a rectangular cut recess.

3. The puncture tool guiding device according to claim 1, wherein a plurality of slits are formed at intervals in an axial direction of the sleeve.

4. The puncture tool guiding device according to claim 3, wherein three or more slits are provided at intervals in the axial direction of the sleeve, and the slits are arranged in a tubular wall of the sleeve in a staggered manner in the axial direction with the central axis of the sleeve therebetween.

5. The puncture tool guiding device according to claim 1, wherein in the sleeve, a through hole extending through the sleeve in parallel with the length direction of the slit is formed separately from the slit.

* * * * *